United States Patent [19]

Johnston

[11] Patent Number: 4,780,413

[45] Date of Patent: Oct. 25, 1988

[54] PRODUCTION OF ANTIVIRAL AGENTS

[75] Inventor: Michael D. Johnston, Beckenham, England

[73] Assignee: Burroughs Wellcome Co., Research Triangle Park, N.C.

[21] Appl. No.: 769,670

[22] Filed: Aug. 26, 1985

Related U.S. Application Data

[63] Continuation of Ser. No. 503,927, Jun. 10, 1983, abandoned.

[30] Foreign Application Priority Data

Jun. 21, 1982 [GB] United Kingdom ............... 8217884

[51] Int. Cl.[4] ..................... C12P 21/00; A61K 45/02
[52] U.S. Cl. ................... 435/69.51; 530/351; 424/85.5; 435/811
[58] Field of Search .................... 435/68, 811; 424/85; 530/351

[56] References Cited

U.S. PATENT DOCUMENTS 3,773,924 11/1973 Ho et al. ............................... 424/85
4,216,203 8/1980 Johnston ............................. 424/85
4,266,024 5/1981 Swetly et al. ....................... 435/68

OTHER PUBLICATIONS

Chemical Abstracts, vol. 81, No. 23, p. 361, Abs. No. 149946t, 1974.

*Primary Examiner*—Blondel Hazel
*Attorney, Agent, or Firm*—Donald Brown

[57] ABSTRACT

An improvement to the process for the production of interferon by adding an inducer to lymphoblastoid cells susceptible to being induced to produce interferon is described wherein the cells are treated with an enhancing agent at, or following, induction. In a preferred aspect the cells are also pretreated, before induction, with a stimulator.

12 Claims, No Drawings

PRODUCTION OF ANTIVIRAL AGENTS

This application is a continuation of application Ser. No. 502,927, filed June 10, 1983, now abandoned.

The present invention relates to improvements in or relating to a process for the production of interferon.

An interferon is a protein which exerts virus non-specific antiviral activity at least in homologous cells through cellular metabolic processes involving synthesis of RNA and protein. Interferons are of interest as potential antiviral and anticancer therapeutic agents. A number of types of interferon are known namely alpha (leucocyte), beta (fibroblast) and gamma (immune) interferons. The present invention is concerned with the production of alpha-interferons.

A source of alpha interferons has been primary human white blood cells, but these cannot provide the abundant amounts of $\alpha$-interferon required for clinical purposes. Recently processes for the production of $\alpha$-interferon from transformed human cells, in particular human lymphoblastoid cells, have been described (Advances in Experimental Medicine and Biology 1978, 110, 61–74; J.Clinical Microbiology 1978, 7, 44–51)and the production of $\alpha$-interferon on a large scale has recently been achieved (Antimicrobial Agents and Chemotherapy, 1979, 15, 420–427). Texas Report Biol.Med., 1981–82, 41, 175–178).

The process for the production of $\alpha$-interferon from human lymphoblastoid cells comprises the steps of growing the lymphoblastoid cells in a suitable medium, inducing the cells to produce interferon by introduction of an inducer, incubation of the cells following induction and recovery of the interferon produced.

A number of techniques have been described for increasing the yield of interferon from such processes.

In one such technique the lymphoblastoid cells are treated for a period of time prior to induction with a pre-treatment agent or 'stimulator'. Thus European Pat. No. 0 000 520 describes a method of increasing the yield of interferon by pre-treatment with a carboxylic acid or a salt thereof, notably sodium butyrate. Similar pre-treatment with a number of other compounds has also been described in the literature (eg. Virology, 1979, 99, 158–166; European Pat. No. 0 008 391).

In such a technique the cells are typically treated for a period, for example about 48 hours, prior to induction, the pre-treatment agent being removed prior to induction.

In an alternative technique an increase in interferon yield is achieved by reducing the temperature of the cultivated cells before, during or following induction (e.g. Proc. Nat. Acad. Sci. USA; 1973, 70, 3909–3913; Japanese J. Microbiology 1974, 18, 217–222; Microbiol. Immunol. 1980, 24, 907–914; J.Gen. Virology, 1981, 56, 163–174).

It has previously been reported in the literature that addition of 'stimulators' (referred to above) at, or following, induction is detrimental to the yield of interferon produced by the cells. This is particularly so in the case of carboxylic acids, such as butyric acid (e.g. Virology, 1979, 99, 158–166; Biochem. Biophys. Res. Commun., 1981 103, 806–812).

It has now been found that the addition of certain compounds (hereinafter referred to as "enhancing agents") at the time of, or shortly after, induction of lymphoblastoid cells produces an increase in the yield of interferon. The invention accordingly provides, in a first aspect, a process for producing interferon which comprises adding an inducer to lymphoblastoid cells which are susceptible to being induced to form interferon, characterised in that, at the time of, or shortly after, induction the cells are treated with an enhancing agent as herein defined.

The lymphoblastoid cells selected for interferon production are chosen according to requirement, thus if the interferon is for administration to humans, then human cells are the type usually selected. The cell used are conveniently Namalawa cells or other suitable lymphoblastoid cell lines. Lines of lymphoblastoid cells that can be serially propagated in culture are readily derived from cultures of peripheral human blood leukocytes by well established methods (see for example, Hope, J. H., Horne, M. K., Scott, W., Int. J. Cancer, 3, pp 857–866 (1978),Hope, J. H., Horne, M. K., Scott, W., Int J. Cancer, 4, pp 255–260 (1969), Chang R. S., Golden H. D., Nature, 234, pp 359–360 (1971). Accordingly, the leukocytes may be obtained from normal or diseased individuals and they may be derived "spontaneously" if the cells are already infected with Epstein-Barr Virus (EBV), or they may be derived from cultures of leukocytes that are not infected with EBV, e.g. umbilical cord blood leukocytes, to which EBV has been added.

Lymphoblastoid cell lines are readily derived from the cells of patients with Burkitt's lymphoma as these are already infected with EBV. One particular line Namalwa, was derived in Stockholm by Prof. G. Klein (Nyormoi, O., Klein G., Adams, A., Dombos, L., Int. J. Cancer, 12, pp 396–408 (1973)) from cells obtained from an African female child of that name. Cells of this line have been found to produce large amounts of interferon when suitably stimulated (Strander, H., Mogesen, K. E., Cantell, K., J.Clin. Microbiol., 1, pp 116–117, (1975); Christophinis, G. J., Steel, C. M. and Finter, N. B., J.Gen.Virol., 1981, 52, 169–171). A subculture of this cell line was obtained from Dr. Ion Gresser (Villejuif, France) in January, 1975. At that time the line was adapted to grow on medium RMPI 1640 with 10% foetal calf serum. At the Wellcome Research Laboratories the cells were adapted to grow on the same medium supplemented with 5–7% serum derived from 6–8 month old calves and they were subcultured two or three times a week during an 18 month period. A Master Bank of these cells now termed Namalwa/WRL were laid down in a number of ampoules which are stored in liquid nitrogen. These cells have been shown to be free from mycoplasma infections and samples have been deposited with the American Type Culture Collection (on 7th July 1978 under No. CRL 1432).

Namalwa/WRL cells were used in the examples hereinafter described but the invention may also applied to other sub-lines of Namalwa cells and other suitable lymphoblastoid cells.

The term 'enhancing agent' as used herein refers to any compounds which, when added at, or shortly after, the time of induction causes a substantial increase in yield of interferon over that obtained when the agent is absent.

A large number of chemically diverse compounds have been found to be effective as enhancing agents. Among these compounds are a number which have previously been described as 'stimulators' for pre-treatment of the cells prior to induction. However, the preferred stimulators, the alkanoic acids (in particular butyric acid) and their salts and steroids (such as dexamethasone), are not enhancing agents and cause a decrease in the yield of interferon if present at or after induction.

Particular compounds found to be effective enhancing agents are also effective in causing differentiation of Friend cells (although not all Friend cell differentiators are effective as enhancing agents).

Effective enhancing agents include:

N-Acetyl-p-amino phenol;

Acetamide and lower alkyl acetamides (such as N-methyl acetamide, N,N-dimethylacetamide, N-ethylacetamide, N,N-diethylacetamide, N-butylacetamide, N-acetyl-6-hydroxyhexylamine);

Acetanilide and lower alkoxyacetanilides (such as p-ethoxy-acetanilide);

Alkylene bisacetamides (in particular $C_4$-$C_8$ alkylene acetamides such as hexamethylene bisacetamide, pentamethylene bisacetamide, heptamethylene bisacetamide);

N,N-Dimethylhexanamide;

Dimethylsulphoxide;

Lower alkylamides (such as propionamide, butyramide);

Lower alkylbenzamides (such as N-methylbenzamide);

Lower alkyl-2-imidazolidinones (such as 1,3-dimethyl-2-imidazolidinones);

1-Lower alkyl-2-pyrollidones (such as 1-methyl-2-pyrollidone, 1-ethyl-2-pyrollidone);

2-Piperidone and 1- lower alkyl-2-piperidones (such as 1-methyl-2-piperidone);

Pyridine-N-oxide; and

Urea derivatives (such as tetramethylthiourea; lower alkyl substituted ureas, eg 1-methylurea, 1-ethylurea, 1-propylurea, 1,1-dimethylurea, 1,3-dimethylurea, 1,3-diethylurea).

Particularly preferred compounds include: N-acetyl-p-aminophenol; hexamethylene bisacetamide; N,N-dimethylacetamide; N-methylacetamide; 1,3-dimethyl-2-imidazolidinone; 1-methylpiperidone; dimethylsulphoxide; 1-methyl-2-pyrollidone; and p-ethoxyacetanilide; tetramethylurea.

Lower alkyl as used herein refers to alkyl residues containing from 1 to 6 preferably 1 to 4, carbon atoms.

In order to produce interferon the selected cells must first be grown under conditions which are suitable and convenient for each cell type or strain as documented in the literature. For example, human lymphoblastoid cells, such as the Namalwa cell line, grow readily in suspension in growth medium, such as RPMI 1640 (Moore, G. E., et. al., 1967 *J. Amer. Med. Assoc.* 199, 519–524) supplemented with serum, for example calf or horse serum, usually at 5%–10% (v/v).

For producing interferon from lymphoblastoid cells, for example Namalwa cells, the cells are first grown in suspension until they have reached an adequate concentration. The concentration, conditions etc. required for interferon production are well known and will be clear to those skill in the art.

It is at this stage that the enhancing agent is added. Ideally the agent is added at the time of induction (ie when the inducing substance, eg Sendai virus, is added to induce interferon production) that is to say the enhancing agent may be incorporated into the medium for cell suspension immediately prior to induction or added to the cell suspension immediately after induction. However, the benefits of the invention may still be obtained if the enhancing agent is added sometime after induction, for example up to about 2 hours thereafter.

The amount of enhancing agent employed will be limited by the toxicity thereof to the cell line, but will be present in an amount effective at producing enhancement of interferon production. The optimum concentration for a balance between toxicity and enhancement of interferon will vary with the particular agent selected but will generally be such as to provide a final concentration of from 0.1 to 500 mM, preferably 1 to 200 mM, most preferably about 5 to 50 mM.

The conditions of induction and subsequent incubation to produce interferon may be effected by any of those known in the art for such a process. For examples the cells may be resuspended in medium RPMI 1640, containing no serum or supplemented with up to 5% v/v serum, to give a final cell concentration of from 0.25 to $6 \times 10^6$ cells/ml, preferably 0.5 to $3 \times 10^6$ cells/ml. A suitable inducer such as a virus, for example Sendai virus (e.g. Johnston, M. D., J.Gen.Viol., 1981, 56, 175–184), is added to the cell suspension to give a final concentration of 5 to 200 Haemagglutination Units per millilitre (HAU/ml), preferably 20 to 50 HAU/ml. After thorough mixing the cell suspension is incubated for a period of 12 to 48 hours at a temperature of from 34° to 37° C. For example at 35° C. the cell culture can conveniently be incubated overnight, during which time interferon is liberated from the cells into the medium. Following incubation the cells are removed by for example centrifugation, leaving a supernatant containing the crude interferon which may, if required, be purified by techniques known in the art.

The increase in yield which may be obtained by use of an enhancing agent as defined herein may be substantial, increases in yield being up to about 5 times those obtained in the absence of such an agent.

The mechanism by which the enhancing agents act is not at this time fully understood. However, the evidence indicates that the rate of interferon production continues to increase for a longer period than is the case when no enhancer is present. This is believed to be a consequence of an extension of time over which interferon mRNA is transcribed, i.e. a true superinduction. The invention accordingly provides in an alternative aspect, a method for the production of interferon which comprises adding an interferon inducer to lymphoblastoid cells which are susceptible to being induced to form interferon, characterised in that, following induction, the period of time during which the rise in the rate of interferon production normally obtained is substantially extended.

By the term "normally obtained" is meant that which is obtained when interferon is prepared from lymphoblastoid cells by those methods well known in the art and without any intervention to alter the period of time wherein the rate of interferon productions is increasing.

The extension of time for the rise in interferon production may be achieved by increasing the time over which interferon mRNA is transcribed, i.e. by superinduction. Conveniently the extension of time may be achieved by means of an enhancing agent, as defined herein, under the conditions defined herein. The invention thus provides a means of increasing the period of interferon production over that which exists if the cells were left to produce interferon by incubation conditions known in the art.

Advantageously the present invention may be combined with techniques known in the art for increasing the yield of interferon from lymphoblastoid cell lines. Thus the techniques of temperature reduction and pretreatment with a stimulator prior to induction may each be combined with the techniques described herein, leading to higher yields of interferon than may be obtained by means of any one technique alone.

In particular the use of a stimulator for pre-treatment of the cells prior to induction (as described in European Pat. Nos. 0 000 520 and 0 008 391 both of which are incorporated herein by reference) has been found to be advantageous.

Where a stimulator also acts as an enhancing agent the same compound may be employed to perform both functions. However it is preferred that the pre-treatment is carried out by the method of European Patent No. 0 000 520, that is to say by means of an alkanoic acid or salt thereof, in particular butyric acid or sodium butyrate.

The invention accordingly provides in a further aspect a method for the production of interferon comprising adding an inducer to lymphoblastoid cells which are susceptible to being induced to form interferon, the cells having been incubated in a medium containing an effective non-toxic amount of a stimulator prior to induction and wherein an enhancing agent, as hereinbefore defined, is added simultaneously with, or shortly after, the time of induction.

The invention also provides, in an alternative aspect a method for the production of interferon comprising adding an inducer to lymphoblastoid cells susceptible of being induced to form interferon, the cells being incubated, prior to induction, in a medium containing an effective, non-toxic amount of a stimulator and wherein the period of time after induction, during which the rise in the rate of interferon production is obtained is substantially extended. The invention is illustrated by the following Examples which are not intended to limit the invention in any way.

EXAMPLE 1

Effect of Enhancing Agents on Interferon Yield

In a series of experiments Namalwa/WRL cells were grown in suspension in RPMI 1640 medium containing 5% adult bovine serum, polymixin and neomycin and sodium bicarbonate for pH control. When the cells reached a concentration of $2 \times 10^6$ cells/ml a portion of the culture was removed and diluted in the same medium to $1 \times 10^6$ cells/ml. Sodium butyrate was added to 1 mM and the cells incubated with stirring at 37° C. for 48 hours.

After this incubation period the cells were recovered by centrifugation at 800×g. The cell pellet was resuspended in RPMI 1640 medium containing 2% adult bovine serum and adjusted to $3 \times 10^6$ cells/ml. Sendai virus was added to 10 haemmagglutination units/ml to induce the formation of interferon. The induced cells were dispersed in volumes of 10 ml into 25 cm² plastic tissue culture flasks. Each flask was treated with a different enhancing agent as indicated in Table I below at the concentration indicated. Two flasks received no additions. Interferon was harvested after 24 hours by centrifuging the cells at 800 xg for 5 min. The clear supernatant medium containing the interferon was acidified to pH 2 and kept at 4° C. for 24 hours before assaying the interferon. The increase in interferon titre against a standard control (wherein no enhancing agent was added) was determined for each enhancing agent. The results are shown in Table I below.

| Enhancing agent added to the induced culture | Final concentration enhancing agent (mM) | Increase in Interferon titre relative to control |
|---|---|---|
| Acetamide | 20 | 2 |
| Acetanilide | 2 | 2 |
| N—acetyl-6-hydroxy hexylamine | 5 | 3 |
| N—butyl acetamide | 5 | 5 |
| butyramide | 10 | 3 |
| N,N—diethyl acetamide | 10 | 4 |
| 1,3-diethyl urea | 5 | 3 |
| N,N—dimethyl acetamide | 5 | 2 |
| N,N—dimethylhexanamide | 3 | 2 |
| 1,3-dimethy-2-imidazolidinone | 2 | 3 |
| dimethylsulphoxide | 140 | 4 |
| 1,1-dimethyl urea | 10 | 2 |
| 1,3-dimethyl urea | 5 | 3 |
| p-ethoxy acetanilide | 2 | 2 |
| N—ethylacetamide | 10 | 3 |
| N—ethyl pyrrolidinone | 5 | 3 |
| ethylurea | 20 | 3 |
| hexamethylenebisacetamide | 5 | 7 |
| p-hydroxyacetanilide | 5 | 3 |
| N—methylacetamide | 10 | 2 |
| N—methylbenzamide | 4 | 3 |
| N—methyl-2-piperidone | 5 | 3 |
| N—methyl-2-pyrrolidinone | 10 | 4 |
| methylurea | 50 | 2 |
| 2-piperidone | 25 | 2 |
| propionamide | 20 | 3 |
| propylurea | 10 | 3 |
| pyridine-N—oxide | 50 | 4 |
| tetramethylthiourea | 5 | 4 |
| tetramethylurea | 8.4 | 6 |

EXAMPLE 2

Effect of Enhancing Agents on Interferon Yield in the presence and absence of butyrate pre-treatment Namalwa/WRL cells, grown as described in Example 1, were diluted in fresh medium to $1 \times 10^6$ cells/ml. The culture was divided equally between two spinner flasks. Sodium butyrate was added to 1 mM to one flask. The second flask received no addition. Both cultures were incubated with stirring for 48 hours. The cells were induced with Sendai virus as described in Example 1. Enhancing agents, as shown in Table II below, were added at the indicated concentrations to induced cultures pretreated and not pretreated with sodium butyrate. The interferon was harvested and prepared for assay as described in Example 1 and the increase in interferon yield against a standard control determined. The results obtained area shown in Table II below.

TABLE II

| Concentration of sodium butyrate used to pretreat Namalwa cells (mM) | Enhancing agent added at induction | Concentration of enchancing agent (mM) | increase in Interferon titre relative to control |
|---|---|---|---|
| 0 | none | — | 1 |
| 0 | acetanilide | 2 | 3 |
| 0 | N,N dimethyl-acetamide | 5 | 3 |
| 0 | dimethylsulphoxide | 140 | 2 |
| 0 | N methylbenzamide | 4 | 3 |
| 0 | tetramethylurea | 8.4 | 6 |
| 1 | none | — | 1 |
| 1 | acetanilide | 2 | 2 |
| 1 | N,N dimethyl-acetamide | 5 | 2 |
| 1 | dimethylsulphoxide | 140 | 2 |
| 1 | N methylbenzamide | 4 | 3 |
| 1 | tetramethylurea | 8.4 | 3 |

EXAMPLE 3

Use of Dimethylsulphoxide as both stimulator and enhancing agent

Namalwa/WRL cells grown as described in Example 1, were diluted in fresh medium to $1 \times 10^6$ cells/ml. The culture was divided equally between two spinner flasks. Dimethyl sulphoxide was added to 140 mM to one flask. The second flask received no addition. Both cultures were incubated with stirring for 48 hours. The cells were centrifuged at 800 x g, resuspended in fresh medium to a concentration of $3 \times 10^6$ cells/ml and induced to the interferon as described in Example 1. Dimethyl sulphoxide was added to 140 mM to one induced culture prepared from cells pretreated with dimethyl sulphoxide and also added at the same concentration of one induced culture prepared from cells not pretreated with dimethyl sulphoxide. After 24 hours the interferon was harvester and prepared for assay as described in Example 1.

| Concentration of dimethyl sulphoxide used to pretreat Namalwa cells (mM) | Concentration of dimethyl sulphoxide added at induction (mM) | Interferon titre ($\log_{10}$ reference units/ml). |
| --- | --- | --- |
| 0 | 0 | 3.55 |
| 140 | 0 | 4.0 |
| 0 | 140 | 3.9 |
| 140 | 140 | 4.3 |

EXAMPLE 4

Kinetics of Interferon production in the presence and absence of an Enhancing Agent and with and without butyrate pretreatment Namalwa/WRL cells, grown as described in Example 1, were diluted ion fresh medium to $1 \times 10^6$. The culture was divided equally between two spinner flasks. Sodium butyrate was added to 1 mM to one flask; the second flask received no addition; both cultures were incubated with stirring for 48 hours. The cells were centrifuged at 800 x g, resuspended in fresh medium to $3 \times 10^6$ cells/ml and induced to make interferon as described in Example 1. Tetramethyl urea was added at 8.4 mM to half the induced cultures prepared from cells pretreated with sodium butyrate and also added to the same concentration to half the induced cultures prepared from cells not pretreated with sodium butyrate. The remaining cultures received no tetramethyl urea. There were, therefore, four groups of inductions comprised of cells pretreated with sodium butyrate and to which tetramethyl urea was either added or not added at the time of induction of interferon with Sendai virus and cells not pretreated with sodium butyrate and to which tetramethyl urea was either added or not added at the time of induction of interferon with Sendai virus. At intervals of two hours one culture from each of the four groups was centrifuged at 800 x g. The medium was removed and the cell pellet drained throughly. The cells were resuspended in the original volume of fresh medium to which tetramethyl urea was then added if it had been present in the medium before centrifugation. After a further two hours incubation the interferon in these same cultures was harvested as described in Example 1.

| Time interval after induction over which Interferon harvested (hours) | Interferon titre ($\log_{10}$ reference units/ml) | | | |
| --- | --- | --- | --- | --- |
| | Namalwa cells not pretreated with sodium butyrate | | Namalwa cells pretreated with 1 mM sodium butyrate | |
| | no Enhancing Agent added at induction | 8.4 mM tetramethyl urea added at induction | no Enhancing Agent added at induction | 8.4 mM tetramethyl urea added induction |
| 0-2 | 0.75 | 0.75 | 1.05 | 1.05 |
| 2-4 | 0.75 | 0.75 | 2.6 | 2.7 |
| 4-6 | 1.8 | 1.7 | 4.05 | 4.2 |
| 6-8 | 2.55 | 2.9 | 4.25 | 4.65 |
| 8-10 | 2.7 | 3.5 | 4.1 | 4.9 |
| 10-12 | 2.8 | 3.7 | 3.95 | 4.65 |
| 12-14 | 2.6 | 3.75 | 3.55 | 4.5 |
| 14-16 | 2.6 | 3.7 | 3.25 | 4.1 |
| 16-18 | 2.45 | 3.55 | 3.15 | 3.95 |

EXAMPLE 5

Effect of Addition of Butyrate at Induction in the presence and absence of Butyrate pretreatment Namalwa/WRL cells, grown as described in Example 1, were centrifuged at $800 \times g$, resuspended in fresh medium to $3 \times 10^6$ cells/ml and induced to form interferon as in Example 1. Immediately after induction of the cells with Sendai virus, sodium butyrate was added to the concentrations drawn in the Table below. The interferon in the medium after 24 hours incubation was harvested as in Example 1.

| Concentration of sodium butyrate added to induced cultures (mM) | Interferon titre $\log_{10}$ reference units/ml |
| --- | --- |
| 0 | 4.38 |
| 0.1 | 4.32 |
| 0.2 | 4.33 |
| 0.5 | 4.27 |
| 1 | 4.17 |
| 2 | 4.14 |
| 5 | 3.93 |
| 10 | 3.83 |

I claim:

1. A process for producing interferon which comprises adding an interferon inducer to lymphoblastoid cells which are susceptible to being induced to form interferon, characterized in that substantially at the time of or shortly after induction the cells are treated with tetramethylurea as an enhancing agent.

2. A process as claimed in claim 1 where in the enhancing agent is present in a concentration of 0.1 to 500 mM.

3. A process as claimed in claim 2 wherein the concentration of the enhancing agent is 1 to 200 mM.

4. A process as claimed in claim 2 wherein the concentration of the enhancing agent is 5 to 50 mM.

5. A process as claimed in claim 1 wherein the enhancing agent is added at the time of induction.

6. A process as claimed in claim 1 wherein the enhancing agent is added within a period of 2 hours after induction.

7. A process as claimed in claim 1 wherein the cells are pretreated with a stimulator prior to induction.

8. A process for production of interferon which comprises adding an interferon inducer to lymphoblastoid cells which are susceptible to being induced to form interferon, the cells being incubated prior to induction, in a medium containing a stimulator, characterised in that, following induction, the period of time during which the rise in the rate of interferon production occurs is substantially extended by the addition of tetramethylurea as an enhancing agent, substantially at the time of or shortly after induction.

9. A process as claimed in claim 8 wherein the enhancing agent is present in a concentration of 0.1 to 500 mM.

10. A process as claimed in claim 8 wherein the enhancing agent is added at the time of induction.

11. A process as claimed in claim 8 wherein the enhancing agent is added within a period of 2 hours after induction.

12. A process as claimed in claim 8 wherein the cells are pretreated with a stimulator prior to induction

* * * * *